United States Patent [19]

Lavacchielli et al.

[11] Patent Number: 5,347,006
[45] Date of Patent: Sep. 13, 1994

[54] METHOD OF PREPARING A POLYMORPH OF TERFENADINE

[76] Inventors: Augusto Lavacchielli, Via Crespi 67, 28100 Novara; Mirco Fornaroli, Via 4 Novembre 50, 28068 Romentino (No); Giovanni Colli, Via Alberio 29, 28066 Galliate (No), all of Italy

[21] Appl. No.: 999,596

[22] Filed: Dec. 31, 1992

[51] Int. Cl.$^5$ .......................................... C07D 211/22
[52] U.S. Cl. .................................................... 546/241
[58] Field of Search ......................................... 546/241

[56] References Cited

U.S. PATENT DOCUMENTS 4,742,175  5/1988  Fawcett et al. ..................... 546/241

FOREIGN PATENT DOCUMENTS 0396100  11/1990  European Pat. Off. ............ 546/241

OTHER PUBLICATIONS

Carr et al., Arzneim-Forsch/Drug Res. 32(II) 9A, 1157-9 (1982).

Primary Examiner—Marianne M. Cintins
Assistant Examiner—Phyllis G. Spivack
Attorney, Agent, or Firm—Fred A. Keire

[57] ABSTRACT

The invention relates to a method for preparing HMP terfenadine comprising the steps of reacting terfenadone free-base with sodium borohydride to yield mixed polymorph terfenadine and crystallizing said mixed polymorph terfenadine from a seeded ester or ketone solvent system to yield substantially pure HMP terfenadine.

9 Claims, No Drawings

METHOD OF PREPARING A POLYMORPH OF TERFENADINE

BACKGROUND OF THE INVENTION

This invention relates to a method of preparing a polymorph of terfenadine. More particularly, the invention relates to a method for reproducibly obtaining substantially pure higher melting point polymorph(s) of terfenadine. "Higher melting point terfenadine" (hereinafter referred to as "HMP terfenadine") is defined as polymorph(s) of terfenadine having a melting point in crystalline form of from about 148.5° C. to about 151° C.

Terfenadine is a histamine $H_1$-receptor antagonist with the chemical name alpha-(p-tert-butylphenyl)-4-(hydroxy-diphenylmethyl)-1-piperidinebutanol, or alpha-(p-tert-butylphenyl)-4-(alpha-hdroxy-alpha-phenlybenzyl)-1-piperidinebutanol. Terfenadine is a nonsedating antihistamine and is the active ingredient in Merrell Dow pharmaceuticals Inc.'s Seldane ® brand pharmaceutical dosage form.

Prior methods of crystallizing terfenadine have produced a product which, while apparently chemically pure, nonetheless exhibits a widely variable melting point. For example, U.S. Pat. No. 3,878,217 discloses alpha-aryl-4-substituted piperidinoalkanol derivatives and methods for their preparation. Terfenadine is an alpha-aryl-4-substituted piperidinoalkanol derivative. Example I of the '217 patent discloses a method for preparing what appears to be a polymorphic mixture of terfenadine (or "mixed polymorph terfenadine") having a melting point of 146.5° C. to 148.5° C. The method disclosed utilizes terfenadone hydrochloride as the starting material and includes the step of adding methanolic potassium hydroxide to render the terfenadone hydrochloride solution basic.

U.S. Pat. No. 4,742,175 discloses methods for the preparation of polymorphic forms of terfenadine having melting points of 149°–151° C. and of about 146°. Crystalline terfenadine having a melting point of 149°–151° C. is prepared using a "lower alkanol solvent".

It is well known that the particular solvent effective in the crystallization of a product is both of fundamental importance to the particular crystallization desired and of low predictability, determinable only by experimentation. See, for example, F.G. Mann et al, *Practical Organic Chemistry*, pp. 13–18, 4th Ed. 1960, and B.S, Furniss et al, *Vogel's Textbook of Practical Organic Chemistry*, pp. 105–113, 4th Ed. 1978.

Polymorphism is the crystallization of the same compound in different crystalline forms. Polymorphic transformations do not involve a molecular change but, rather a physical change. Polymorphism is very common in the pharmaceutical industry. Drugs that crystallize in different forms exhibit a wide range of chemical and physical properties, including different melting points and spectral properties. The crystalline form of drugs is particularly important since the dissolution rates, bioavailability, chemical reactivity and physical stability of a even a chemically pure solid state drug can vary with the particular crystalline form of the drug. Haleblian, J. and McCrone, W.C. (1969), *J.Pharm.Sci.*, 58, 911; Byrn, S. (1976), *J.Pharm.Sci.*, 65, 1. Methods for the reproducible production of substantially polymorphically pure drugs are therefore very much in demand.

Applicants have discovered methods for the reproducible preparation of substantially pure HMP terfenadine on both laboratory and commercial production scales. These methods permit the use of free-base terfenadone as the starting material and therefore do not require the addition of caustic hydroxides such as methanolic potassium hydroxide to neutralize solutions of terfenadone hydrochloride. Moreover, unlike prior art methods, applicants'methods utilize a ketone or ester solvent in the crystallization of the final product from crude terfenadine.

OBJECTS OF THE INVENTION

It is a primary object of this invention to provide a method for producing substantially pure HMP terfenadine.

It is an additional object of this invention to provide a method for the preparation of HMP terfenadine using free-base terfenadone as the starting material.

It is a further object of this invention to provide a method for the preparation of HMP terfenadine which does not require the use of caustic hydroxides such as methanolic potassium hydroxide.

It is a still further object of this invention to provide a method for the preparation of HMP terfenadine using a ketone or ester as the solvent in the crystallization of the final product from crude terfenadine.

It is a still further object of this invention to provide a reliable, reproducible method for a commercial production scale preparation of HMP terfenadine.

SUMMARY OF THE INVENTION

Broadly, the objects of the invention are achieved in a method of preparing HMP terfenadine from terfenadone free-base involving crystallization in a ketone or ester solvent system. More specifically, HMP terfenadine is manufactured in a multi-step process including the steps of converting terfenadone to terfrenadine and re-crystallizing the resulting terfenadine in a seeded ketone or ester solvent system to yield substantially pure HMP terfenadine.

DETAILED DESCRIPTION OF THE INVENTION

HMP terfenadine is produced in accordance with the following reaction scheme:

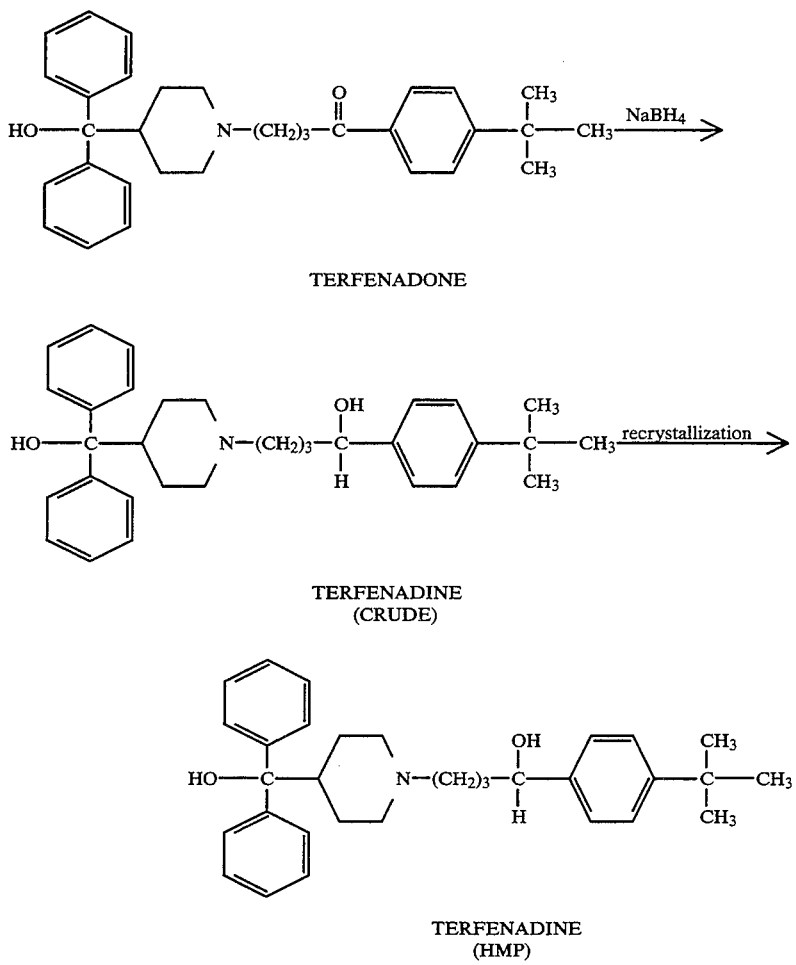

TERFENADONE

TERFENADINE
(CRUDE)

TERFENADINE
(HMP)

The initial step in the preparation of HMP terfenadine is to synthesize the starting material, terfenadone free-base. Crude or chemically pure mixed polymorph terfenadine is then synthesized from the terfenadone free-base. Finally, recrystallization of the resulting crude or chemically pure mixed polymorph terfenadine under the reaction conditions specified below results in high yields of substantially pure HMP terfenadine.

Solutions of terfenadine in a ketone or ester solvent are prepared conventionally. Typically, solutions of a solid to be recrystallized are highly concentrated, near the saturation point of the solute in solution. Moreover, solutions to be recrystallized are usually heated at about the reflux temperature of the solution. Similarly, the hot, concentrated solution is generally filtered prior to crystal formation in order to remove any insoluble particulate matter.

The solutions of terfenadine to be recrystallized are prepared conventionally by adding a chemically pure or crude polymorphic mixture of terfenadine to the solvent, with stirring or agitation. HMP terfenadine may be produced from terfenadine solids containing various impurities, including but not limited to organic impurities and inorganic salts.

Preparation of Terfenadone

The "free base" form of the Terfenadone starting material is prepared by reacting azacyclonol with 4-chloro-1-[4-(1,1-dimethylethyl)phenyl]-1-butanone by methods known in the art (cfr A. A. Cart and D. R. Meyer - Arzneim. Forsch. / Drug Res. 32 (II), Nr 9a 1157-59 (1982), and U.S. Pat. No. 3,806,526.

Preparation of Crude Terfenadine From Terfenadone

Methanol and terfenadone are loaded into a stainless steel reactor or flask and warmed up to reflux in order to obtain a clear solution. The solution is then cooled with water to about 15° C. and sodium borohydride is slowly added. The solution is stirred and cooled with circulating water as the sodium borohydride is added. The solution is then heated to reflux. Once the reaction is completed, the solution is distilled and cooled with circulating water until the product precipitates. Water is added to the reactor and the precipitated terfenadine cake is washed, cooled with circulating water, and centrifuged. The wet product is then dried at about 70° C.

Recrystallization of Crude Terfenadine From Acetone to Yield Higher Melting Point Terfenadine Generally, crude dry terfenadine, an ester or ketone solvent, and a small quantity of diatomaceous earth (an inert substance also known as "filter AID") are loaded into a stainless steel reactor or flask. The solution is heated and refluxed for about ½ hour, then filtered and sent to a glass-lined reactor. The solution is again heated to reflux until a complete solution is obtained, seeded with a small quantity of HMP terfenadine at a temperature of at least 45° C., then cooled. The source of HMP terfenadine used to seed the solution is the USP Terfenadine Reference Standard, based upon which a small amount of higher melting point terfenadine is produced on a laboratory scale.

When the mass begins to thicken, the solution is cooled with circulating water down to about 15° to 20° C., then allowed to stand overnight. The precipitated terfenadine cake is washed with a ketone or ester solvent, centrifuged, and the product is dried at about 70° C. The mother liquors are then concentrated by distilling, and a second crop of product precipitates out upon cooling. The product is then washed with a ketone or ester solvent, centrifuged, and dried, resulting in an overall yield of about 94–95%. The resulting product is substantially pure HMP terfenadine. Subsequent crops may be precipitated in a similar fashion. Finally, the solvents from the mother liquors may be recovered by simple distillation and recycled for use in subsequent syntheses. Suitable ketone solvents include, for example, acetone, methylethylketone, 2-butanone, and methylisobutylketone; of these methylethylketone and acetone are preferred, with acetone being the ketone solvent of choice. Suitable ester solvents include, for example, methylacetate, ethylacetate, and isopropyl acetate; of these methylacetate and ethylacetate are preferred, with ethylacetate being the ester solvent of choice.

The invention is further illustrated by the examples appearing below. As can be seen from the examples, the best yields of HMP terfenadine were achieved by recrystallization in acetone. Accordingly, ketone solvents are the first choice and acetone is the preferred solvent.

In the following examples and throughout this specification, the melting point of a solid (also known as the "melting range" or "melting temperature") is determined according to standard United States Pharmacopea ("USP") procedures for determining the melting range or temperature for Class I solids, described at USP XXII <741> "Melting Range or Temperature", pages 1588–1589 (1992).

EXAMPLE 2

0.5 kg. (1.06 moles) of crude, mixed polymorph terfenadine was charged to a 5 liter flask, to which 2.88 liters of ethylacetate, 0.08 liters of water and 2.5 g of diatomaceous earth were added.

The terfenadine was brought into solution by warming to reflux. The solution was filtered at a temperature not lower than 65° C. and then transferred into another 5 liter flask. The filtered solution was then cooled to 50° C. and seeded with a few crystals of higher melting polymorph terfenadine (m.p. 149°–150° C.). Seeding was effected at a temperature between 45° C. and 50° C., when the solution was still clear. The product was then allowed to crystallize from solution. When the mass began to thicken, it was cooled with a water bath to 15° C.

The solution was then filtered and the resulting cake washed with a small quantity of ethylacetate. This was followed by drying at 70° C. for 180 minutes. The resulting product was 378 g of terfenadine having a melting point of 149° to 150° C.

EXAMPLE 2

0.5 kg. (1.06 moles) of crude, mixed polymorph terfenadine was charged to a 5 liter flask, to which 3 liters of anhydrous ethylacetate and 2.5 g of diatomaceous earth were added.

The terfenadine was brought into solution by warming to reflux. The solution was filtered at a temperature not lower than 65° C. and then transferred into another 5 liter flask. The filtered solution was then cooled to 50° C. and seeded with few crystals of higher melting polymorph terfenadine (m.p. 149°–150° C.). Seeding was effected at a temperature between 45° C. and 50° C., when the solution was clear. The product was then allowed to crystallize from solution. When the mass began to thicken, it was cooled in a water bath to 15° C.

The solution was then filtered and the resulting cake washed with a small quantity of ethylacetate. Filtering was followed by drying at 70° C. for 180 minutes. The resulting product was 380 grams of terfenadine having a melting point of 148.8° to 149.8° C.

EXAMPLE 3

0.5 kg. (1.06 moles) of crude, mixed-polymorph terfenadine was charged to a 5 liter flask, to which 4 liters of acetone and 2.5 g of diatomaceous earth were added.

The terfenadine was brought into solution by warming to reflux. The solution was filtered at a temperature not lower than 55° C. and then transferred into another 5 liter flask. The filtered solution was then cooled to 50° C. and seeded with few crystals of higher melting polymorph terfenadine (m.p. 149°–150° C.). Seeding was effected at a temperature between 45° C. and 50° C., when the solution was still clear. The product was then allowed to crystallize from solution. When the mass began to thicken, it was cooled in a water bath to 15° C.

The solution was then filtered and the resulting cake washed with a small quantity of ethylacetate. Filtering was followed by drying at 70° C. for 180 minutes. The resulting product was 387.5 grams of terfenadine having a melting point of 149.4° to 50.4° C.

EXAMPLE 4

A 1,000 liter stainless steel reactor was loaded with 80 kg. (169 moles) of crude, dry, mixed polymorph terfenadine, 650 liters (520 kg.) of acetone, and 0.4 kg. of diatomaceous earth.

The terfenadine was brought into solution by heating and refluxing for about 30 minutes. The solution was then filtered through a pre-heated filter press and charged to an 800 liter glass-lined reactor. The solution was again heated until a complete solution was obtained, then cooled to 50° C. For crystallization, the solution was then seeded with a small quantity of HMP terfenadine crystals at a temperature above 45° C. When the mass began to thicken, it was cooled to about 15°–20° C., and allowed to stand overnight.

The resulting precipitate cake was then centrifuge-washed with acetone, resulting in a yield of 75 kg. of wet product, corresponding to about 62 kg. (131 moles) of dry product following drying at 70° C.

The remaining acetonic mother liquors (450 liters or 360 kg.) were then concentrated by distilling, and a second crop of product precipitated out upon cooling as described previously. The product was then washed with acetone and dried, resulting in about 15 kg. of wet second crop. The wet second crops from several charges were then combined and crystallized as described previously.

What is claimed is:

1. A method for preparing HMP terfenadine comprising the steps of:
   (a) reacting terfenadone free-base with sodium borohydride to yield mixed polymorph terfenadine; and (b) crystallizing said mixed polymorph terfenadine from a seeded ester or ketone solvent system to yield substantially pure HMP terfenadine.

2. A method as recited in claim 1, wherein said solvent is selected from the group consisting of: acetone; methylethylketone; 2-butanone; methylisobutylketone; methylacetate; ethylacetate; and ispropylacetate.

3. A method as recited in claim 1, wherein said solvent is acetone.

4. A method for preparing HMP terfenadine comprising the steps of:
(a) reacting azacyclonol with 4-chloro-1-[4-(1,1-dimethylethyl)phenyl]-1-butanone to yield terfenadone free-base;
(b) reacting said terfenadone free-base with sodium borohydride to yield mixed polymorph terfenadine; and
(c) crystallizing said mixed polymorph terfenadine from a seeded ester or ketone solvent system to yield substantially pure HMP terfenadine.

5. A method as recited in claim 4, wherein said solvent is selected from the group consisting of: acetone; methylethylketone; 2-butanone; methylisobutylketone; methylacetate; ethylacetate; and ispropylacetate.

6. A method as recited in claim 4, wherein said solvent is ethylacetate.

7. A method for preparing HMP terfenadine which comprises dissolving terfenadine in an ester or ketone solvent, heating the solution at about its reflux temperature, seeding with an effective amount of HMP terfenadine to cause crystallization, and cooling and collecting the crystalline product.

8. A method for preparing HMP terfenadine comprising the steps of:
(a) introducing mixed polymorph terfenadine into a first reaction vessel together with an effective amount of ethylacetate and an effective amount of diatomaceous earth;
(b) heating and refluxing said terfenadine, ethylacetate and diatomaceous earth at a temperature effective to bring said terfenadine into solution;
(c) filtering and transferring said solution into a second reaction vessel;
(d) cooling said solution;
(e) seeding said solution with an effective amount of HMP terfenadine; and
(f) further cooling said solution and collecting the resulting HMP terfenadine product.

9. A method for preparing HMP terfenadine comprising the steps of:
(a) introducing mixed polymorph terfenadine into a reaction vessel together with an effective amount of acetone and an effective amount of diatomaceous earth;
(b) heating and refluxing said terfenadine, acetone and diatomaceous earth at a temperature effective to bring the terfenadine into solution;
(c) filtering and transferring said solution into a second reaction vessel;
(d) cooling said solution;
(e) seeding said solution with an effective amount of HMP terfenadine; and
(f) further cooling said solution and collecting the resulting HMP terfenadine product.

* * * * *